United States Patent
Hebrank et al.

[11] Patent Number: 5,900,929
[45] Date of Patent: *May 4, 1999

[54] METHOD AND APPARATUS FOR SELECTIVELY INJECTING POULTRY EGGS

[75] Inventors: John H. Hebrank, Durham; Daniel T. DePauw, Raleigh, both of N.C.

[73] Assignee: Embrex, Inc., Research Triangle Park, N.C.

[*] Notice: This patent is subject to a terminal disclaimer.

[21] Appl. No.: 09/008,664

[22] Filed: Jan. 16, 1998

Related U.S. Application Data

[63] Continuation-in-part of application No. 08/785,689, Jan. 17, 1997, Pat. No. 5,745,228.

[51] Int. Cl.[6] .................................................. G01N 33/08
[52] U.S. Cl. .............................................. 356/52; 356/53
[58] Field of Search ............................ 356/52, 53, 55–58

[56] References Cited

U.S. PATENT DOCUMENTS

| | | |
|---|---|---|
| 3,377,989 | 4/1968 | Sandhage et al. . |
| 3,486,982 | 12/1969 | Noren . |
| 3,540,824 | 11/1970 | Fonda et al. ................................ 356/53 |
| 3,616,262 | 10/1971 | Coady et al. . |
| 4,040,388 | 8/1977 | Miller . |
| 4,458,630 | 7/1984 | Sharma et al. . |
| 4,469,047 | 9/1984 | Miller . |
| 4,593,646 | 6/1986 | Miller et al. . |
| 4,671,652 | 6/1987 | van Asselt et al. ......................... 356/66 |
| 4,681,063 | 7/1987 | Hebrank . |
| 4,903,635 | 2/1990 | Hebrank . |
| 4,914,672 | 4/1990 | Hebrank ................................ 374/124 |
| 4,955,728 | 9/1990 | Hebrank ................................ 374/124 |
| 4,978,225 | 12/1990 | Reimer ................................... 356/432 |
| 5,017,003 | 5/1991 | Keromnes et al. ....................... 356/53 |
| 5,321,491 | 6/1994 | Summers et al. ......................... 356/53 |
| 5,745,228 | 4/1998 | Hebrank et al. .......................... 356/53 |

FOREIGN PATENT DOCUMENTS 969581 9/1964 United Kingdom .

OTHER PUBLICATIONS

Product Brochure—EPM 650, Automatic Candling and Transfer Machine, Innovatec, Page Nos. Not Available, Date Not Available.

Product Brochure—The Invoject® Egg Injection System: Setting the New Worldwide Standard, EMBREX, Inc., Pg. Nos. Not Available, Date Not Available.

K. Das, et al., Detecting Fertility of Hatching Eggs Using Machine Vision I. Histogram Characterization Method, *American Society of Agricultural Engineers* 35(4) pp. 1335–1341 (1992).

*Primary Examiner*—Robert H. Kim
*Assistant Examiner*—Amanda Merlino
*Attorney, Agent, or Firm*—Myers Bigel Sibley & Sajovec

[57] ABSTRACT

A method for distinguishing live from dead poultry eggs comprises: (a) providing a light source (preferably an infrared light source) and a light detector in opposite facing relation to one another; (b) passing an egg between the light source and light detector; (c) switching the light source at a frequency greater than 100 cycles per second while passing the egg between the light source and the light detector; and (d) detecting light that passes through the egg from the light source with the light detector. Preferably, the egg is passed between the light source and the light detector without making contact therewith. And the method preferably further comprises the step of electronically filtering the signal detected by the light detector to distinguish light emitted from the light source from ambient light. Steps (b) through (d) may be repeated at a rate of at least one egg per second. Apparatus for carrying out the foregoing method is also provided. A method of selectively injecting only eggs identified as suitable for injection, and apparatus for carrying out such a method, is described.

24 Claims, 11 Drawing Sheets

FIG. 1
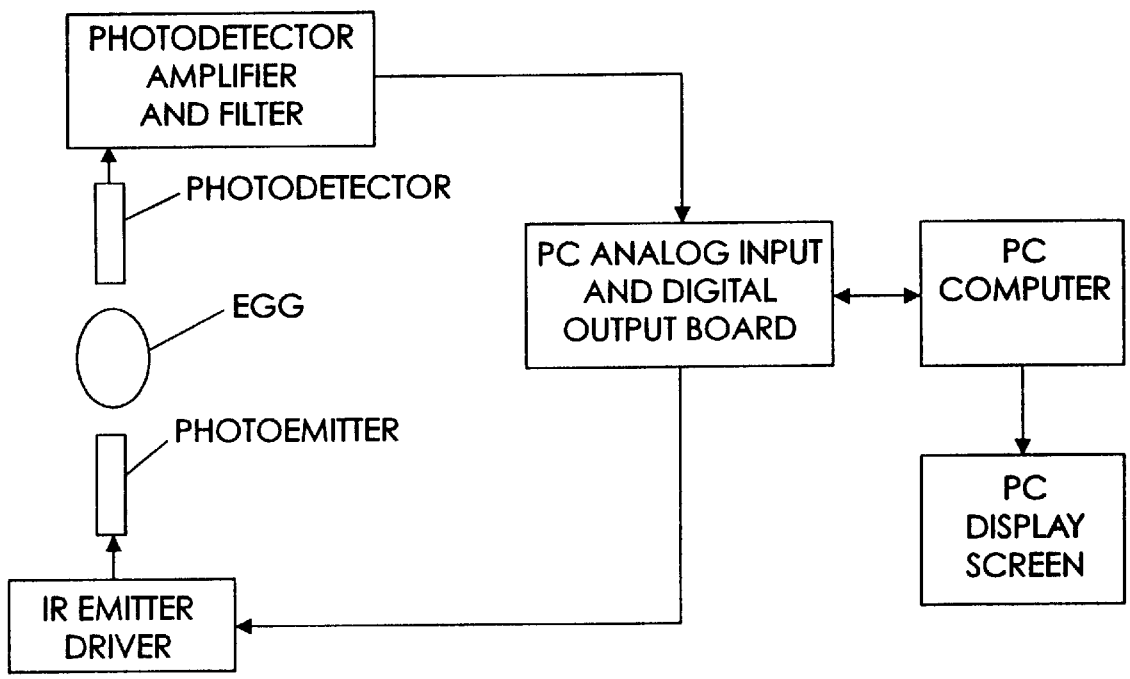
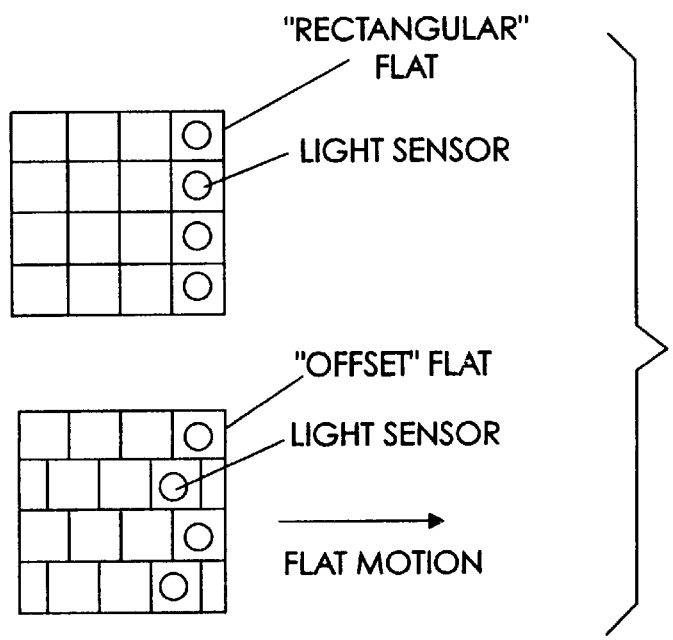
FIG. 2

METHOD AND APPARATUS FOR SELECTIVELY INJECTING POULTRY EGGS

RELATED APPLICATIONS

This application is a continuation-in-part of application Ser. No. 08/785,689, filed Jan. 17, 1997, now U.S. Pat. No. 5,745,228.

FIELD OF THE INVENTION

The present invention concerns methods and apparatus for candling poultry eggs, and in particular concerns methods and apparatus for candling poultry eggs with light that is pulsed or cycled at a frequency different from, and preferably higher than, ambient light.

The present invention further concerns methods and apparatus for injecting a plurality of eggs, where each egg is identified as suitable for injection or non-suitable for injection, and only those identified as suitable for injection are then injected with a treatment substance.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with poultry eggs, although egg shells appear opaque under most lighting conditions, they are in reality somewhat translucent, and when placed in front of a direct light, the contents of the egg can be observed.

In most practices, the purpose of inspecting eggs, particularly "table eggs" for human consumption, is to identify and then segregate those eggs which have a significant quantity of blood present, such eggs themselves sometimes being referred to as "bloods" or "blood eggs." These eggs are less than desirable from a consumer standpoint, making removal of them from any given group of eggs economically desirable.

U.S. Pat. Nos. 4,955,728 and 4,914,672, both to Hebrank, describe a candling apparatus that uses infrared detectors and the infrared radiation emitted from an egg to distinguish live from infertile eggs.

U.S. Pat. No. 4,671,652 to van Asselt et al. describes a candling apparatus in which a plurality of light sources and corresponding light detectors are mounted in an array, and the eggs passed on a flat between the light sources and the light detectors.

In many instances is desirable to introduce a substance, via in ovo injection, into a living egg prior to hatch. Injections of various substances into avian eggs are employed in the commercial poultry industry to decrease post-hatch mortality rates or increase the growth rates of the hatched bird. Similarly, the injection of virus into live eggs is utilized to propagate virus for use in vaccines. Examples of substances that have been used for, or proposed for, in ovo injection include vaccines, antibiotics and vitamins. Examples of in ovo treatment substances and methods of in ovo injection are described in U.S. Pat. No. 4,458,630 to Sharma et al. and U.S. Pat. No. 5,028,421 to Fredericksen et al., the contents of which are hereby incorporated by reference as if recited in full herein. The selection of both the site and time of injection treatment can also impact the effectiveness of the injected substance, as well as the mortality rate of the injected eggs or treated embryos. See, e.g., U.S. Pat. No. 4,458,630 to Sharma et al., U.S. Pat. No. 4,681,063 to Hebrank, and U.S. Pat. No. 5,158,038 to Sheeks et al. U.S. Patents cited herein are hereby incorporated by reference herein in their entirety.

In ovo injections of substances typically occur by piercing the egg shell to create a hole through the egg shell (e.g., using a punch or drill), extending an injection needle through the hole and into the interior of the egg (and in some cases into the avian embryo contained therein), and injecting the treatment substance through the needle. An example of an injection device designed to inject through the large end of an avian egg is disclosed in U.S. Pat. No. 4,681,063 to Hebrank; this device positions an egg and an injection needle in a fixed relationship to each other, and is designed for the high-speed automated injection of a plurality of eggs. Alternatively, U.S. Pat. No. 4,458,630 to Sharma et al. describes a bottom (small end) injection machine.

In commercial poultry production, only about 60% to 90% of commercial broiler eggs hatch. Eggs that do not hatch include eggs that were not fertilized, as well as fertilized eggs that have died (often classified into early deads, mid deads, rots, and late deads). Infertile eggs may comprise from about 5% up to about 25% of all eggs set. Due to the number of dead and infertile eggs encountered in commercial poultry production, the increasing use of automated methods for in ovo injection, and the cost of treatment substances, an automated method for identifying, in a plurality of eggs, those eggs that are suitable for injection and selectively injecting only those eggs identified as suitable, is desirable.

U.S. Pat. No. 3,616,262 to Coady et al. discloses a conveying apparatus for eggs that includes a candling station and an inoculation station. At the candling station, light is projected through the eggs and assessed by a human operator, who marks any eggs considered non-viable. Non-viable eggs are manually removed before the eggs are conveyed to the inoculating station.

SUMMARY OF THE INVENTION

A first aspect of the present invention is a method for distinguishing live from infertile, including dead, poultry eggs. The method comprises: (a) providing a light source (preferably an infrared light source) and a light detector in opposite facing relation to one another; (b) passing an egg between the light source and light detector; (c) switching the light source at a frequency greater than 100 cycles per second (and preferably at a frequency greater than 200 or 400 cycles per second) while passing the egg between the light source and the light detector; and (d) detecting light that passes through the egg from the light source with the light detector. Preferably, the egg is passed between the light source and the light detector without making contact therewith. The method preferably further comprises the step of electronically filtering the signal detected by the light detector to distinguish light emitted from the light source from ambient light. Steps (b) through (d) may be repeated at a rate of at least one egg per second.

A second aspect of the present invention is an apparatus for distinguishing live from infertile poultry eggs. The apparatus comprises an egg carrier, a light measuring system, and a switching circuit. The light measuring system has a light source (preferably an infrared light source) positioned on one side of the egg carrier and a light detector positioned on the other side of the egg carrier opposite the light source. The switching circuit is operatively associated with the light source for cycling the intensity of the light source at a frequency greater than 100 cycles per second, and preferably at a frequency greater than 200 or 400 cycles per second. The egg carrier is configured to carry the eggs between the light source and the light detector in non-contacting relationship therewith. An electronic filter operatively associated with the light detector is configured to distinguish light emitted from the light source from ambient light (i.e., by filtering out higher and/or lower frequency light signals detected by the detector).

A preferred embodiment may also include an optical filter positioned in front of the light detector for filtering ambient light. A drive system may be operatively associated with the egg carrier, with the drive system configured to pass eggs between the light source and the light detector at a rate of at least 1 egg per second. Typically, the egg carrier is configured to carry at least two rows of eggs in side-by-side relationship to one another; here the apparatus comprises a plurality of the light measuring systems positioned in operative association with each of the rows of eggs, and the switching circuit preferably cycles adjacent ones of the light sources at a time or frequency different from one another. Specifically, pulsing or cycling the light at rates of a thousand or more times per second (typically 2000 times per second) allows measuring all eggs in a row of seven within less than 10 milliseconds, so that moving eggs can be sampled at 0.1 second intervals. Eggs moving at 10 inches/second can be sampled at 0.1 inch intervals.

A personal computer or other programmable or non-programmable circuitry may serve as a data collection means operatively associated with the light detectors for storing data associated with the eggs, in which case the switching circuit is operatively associated with the data collection means so that data is collected from each of the light detectors in a cycle corresponding to the cycle of the corresponding light source. Specifically, individual sensors are sampling corresponding emitters that are activated. Furthermore, by taking the difference of successive samples, while a corresponding emitter is on and then off, ambient light can largely be rejected. Rejection of changing ambient light levels, such as from fluorescent lamps, is increased as sampling intervals are made closer in time.

A further aspect of the present invention is an automated apparatus for classifying each egg in a plurality of eggs as either suitable for injection or non-suitable for injection, and selectively injecting only those eggs identified as suitable for injection. The apparatus includes classifying means for classifying each egg as suitable or non-suitable. The classifying means is operatively connected to control means and is capable of generating a classification signal that indicates whether an egg is suitable or non-suitable for injection. Conveying means carry a plurality of eggs in a fixed relationship past the classifier, so that a classification signal for each egg is provided to the control means; the control means receives the classification signal and generates a selective injection signal which is transmitted to injection means. The classification of eggs as suitable or non-suitable may be based on distinguishing fertile from non-fertile eggs, or based on distinguishing live from non-live eggs.

A further aspect of the present invention is a method for selectively injecting, in a plurality of avian eggs, only avian eggs classified as suitable for injection. The method comprises providing means for classifying whether an egg is suitable for injection or not, the classification means operatively connected to control means and capable of generating a classification signal that indicates whether an egg is suitable for injection. A plurality of eggs in a fixed relationship to each other is conveyed past the classification means, and a classification signal associated with each egg is provided to the control means. The control means receives the classification signal and generates a selective injection signal, so that injection means operatively connected to the control means injects only those eggs classified as suitable for injection.

The present invention is explained in greater detail in the drawings herein and the specification set forth below.

BRIEF DESCRIPTION OF THE DRAWINGS

FIG. 1 is a block diagram of a cycled light source control and detector processing for a egg candling in accordance with the present invention;

FIG. 2 shows a top view of a rectangular flat of eggs and an offset flat of eggs to be candled by the method of the present invention;

DETAILED DESCRIPTION OF THE PREFERRED EMBODIMENTS

Figure 3:
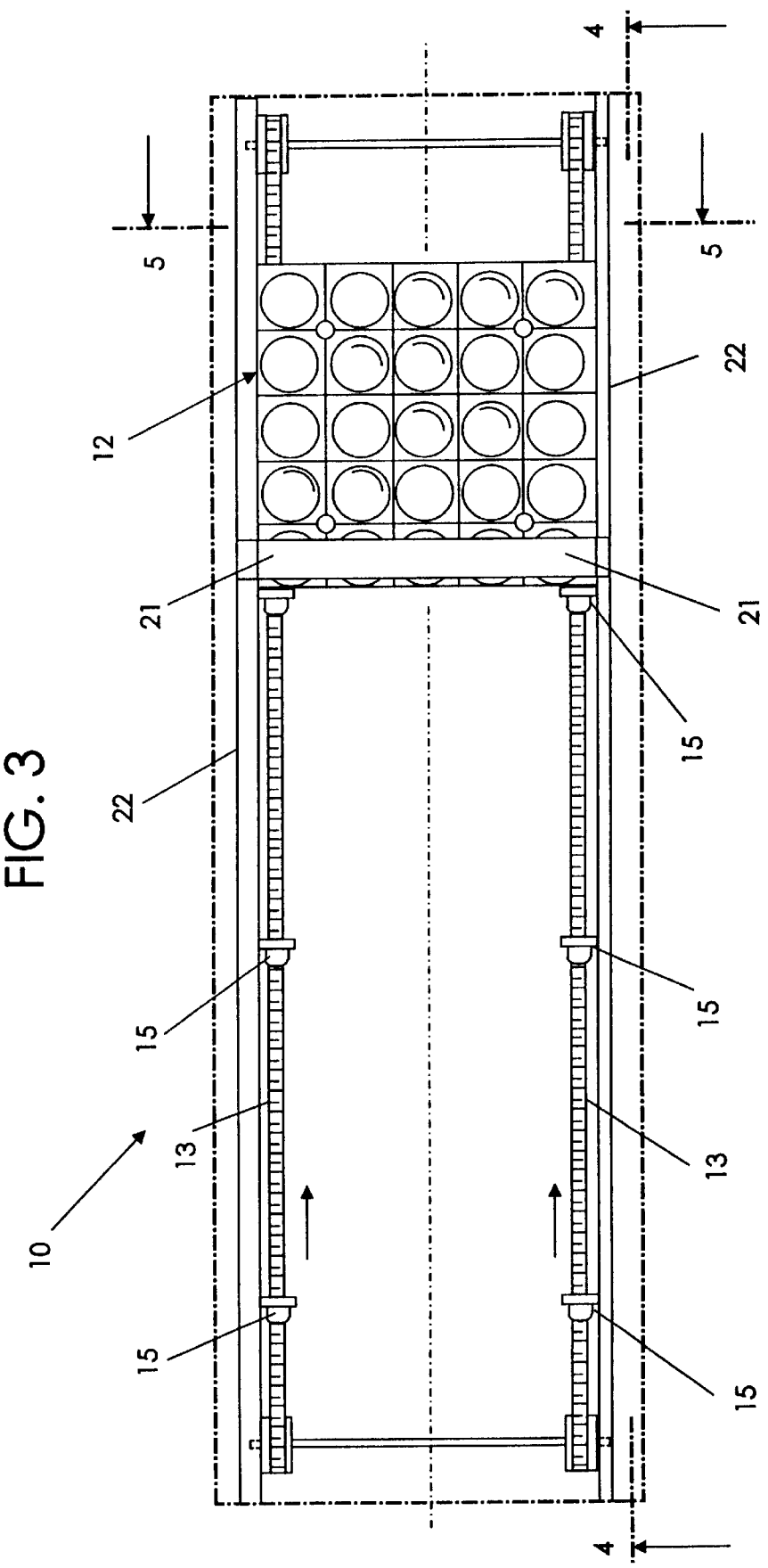
FIG. 3 is a top plan view of an apparatus of the present invention.

The present invention may be carried out with any types of eggs, including chicken, turkey, duck, geese, quail, and pheasant eggs. Chicken eggs are particularly preferred.

The term "cycled" as used herein refers to the switching of the light source or emitter on and off (for example, fluorescent or mercury vapor lights on normal house current are said to be cycled at 60 or 120 cycles per second, and not to the wavelength of the light itself).

FIGS. 1–2 schematically illustrate apparatus that can be used to carry out the method of the present invention. In overview, with reference to FIG. 1, an apparatus of the invention comprises a photodetector associated with a photodetector amplifier and filter circuit, which is in turn associated with a PC analog input board, and a photoemitter (an infrared emitter) associated with an IR emitter driver circuit, in turn associated with a digital output board. The photoemitter and photodetector are positioned to be on opposite sides of an egg: as illustrated, the photodetector is above and the photoemitter is below the egg, but these positions are not critical and could be reversed, or the emitter and detector placed in a different orientation, so long as light from the emitter illuminates the egg to the detector. The input and output board are installed in a personal computer, with operation of the system monitored on the display screen of the PC computer. In operation, the method of the present invention uses time to allow accurate measurement of the light from a single egg. Light is generated in short bursts from each photoemitter (e.g., 50 to 300 microseconds) and the corresponding photodetector only monitors while its corresponding photoemitter is operational. To reduce the effect of ambient light, the output of a photodetector when no light is on is subtracted from the reading when the light is on. In one embodiment, light is generated in a short burst from a photoemitter, and the corresponding photodetector monitors the light level immediately before, during, and immediately after the burst of light is generated. A flat of eggs is continuously "scanned" as it moves through the identifier with each detector-source pair active only while at least adjacent, and preferably all other, pairs are quiescent.

As indicated in FIG. 2, the method and apparatus of the invention are particularly adapted for use with "flats" of eggs. Any flat of eggs with rows of eggs therein may be used, and while five rows are illustrated in the two flats shown schematically in FIG. 2, the flat may contain any number of rows, such as seven rows of eggs, with rows of six and seven being most common. Eggs in adjacent rows may be parallel to one another, as in a "rectangular" flat, or may be in a staggered relationship, as in an "offset" flat. Examples of suitable commercial flats include, but are not limited to, the "CHICKMASTER 54" flat, the "JAMESWAY 42" flat and the "JAMESWAY 84" flat (in each case, the number indicates the number of eggs carried by the flat).

Figure 4:
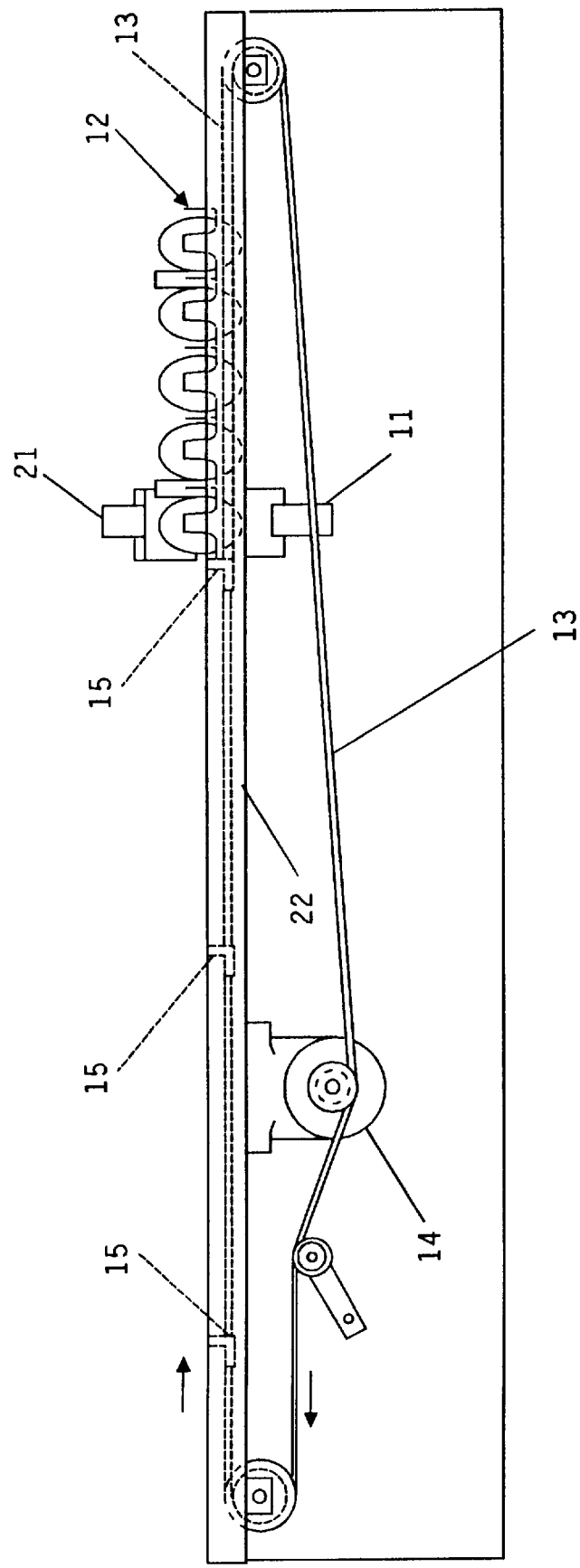
FIG. 4 is an elevational view taken along lines 4—4 of FIG. 3.
Figure 5:
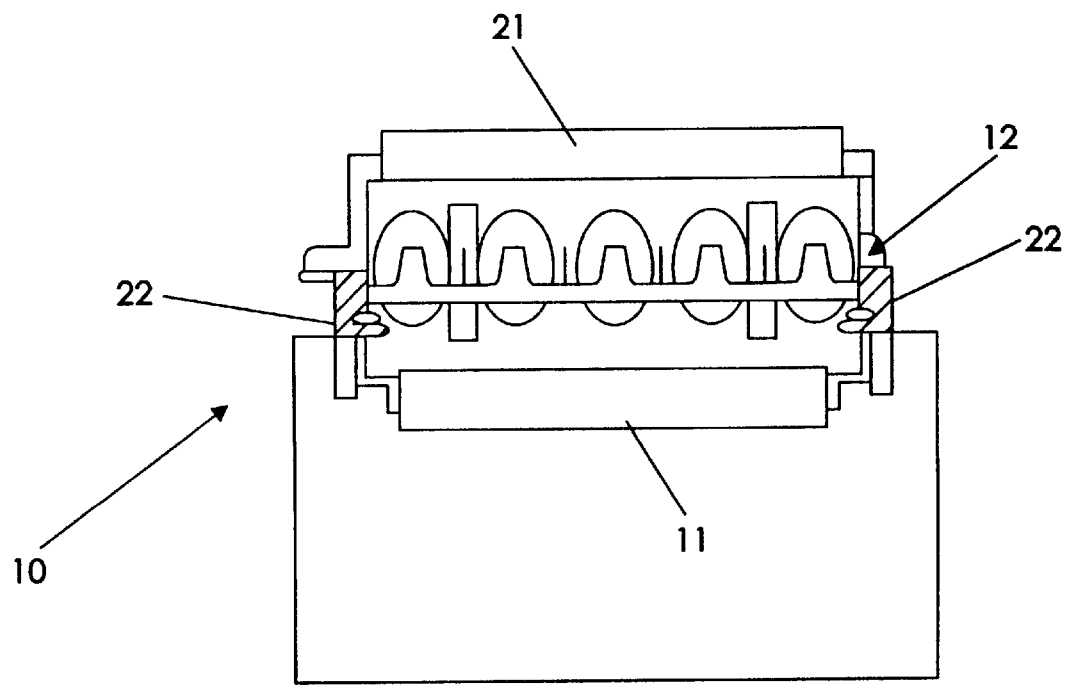
FIG. 5 is an elevational view taken along lines 5—5 of FIG. 3.

FIGS. 3–5 show an apparatus generally designated as 10 that can be used to practice the method of the invention. Apparatus 10 includes an infrared light emitter mounting block 11, an infrared light detector mounting block 21, and a conveyor system as discussed below.

As illustrated, the fixed array of eggs comprises an open bottom setting flat 12 of eggs. The flat 12 carries twenty-five eggs in an array of five rows of five eggs each and rides on a conveyor means which is shown in the form of drive chains 13, chain drive motor 14 and chain drive dogs 15 that moves the flat along the guide rails 22 adjacent the path of the chain 13. In an alternate, preferred embodiment, the chain drive and dogs are replaced with a pair of polymeric conveyor belts riding on support rails, which conveyor belts are ⅜ inch diameter and ride on 0.5 inch frames. Such belts are as found on egg injection equipment, particularly the EMBREX INOVOJECT® egg injection apparatus, and are desirable for their comparability with operator safety and corrosion resistance. Egg flats are typically moved at rates of 10 to 20 inches per second.

Figure 6:
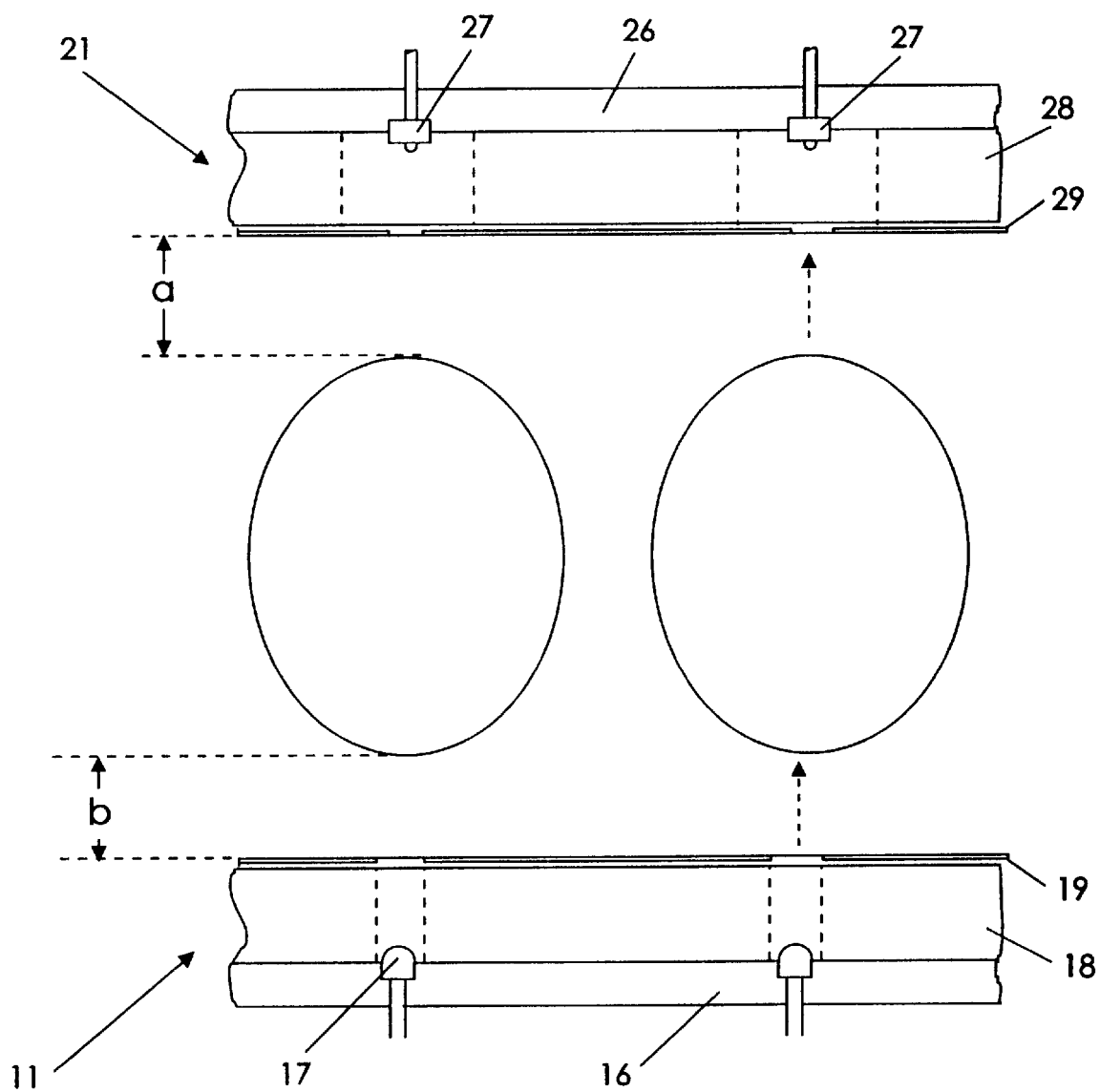
FIG. 6 is a detail view of the light source mounting block and the light detector mounting block.

FIG. 6 illustrates the construction of the infrared light emitter mounting block 11 and the infrared light detector mounting block 21. The infrared light emitter mounting block 11 is comprised of an opaque back plate 16 with the infrared emitters 17 (Photonics Detectors, Inc. Part number PDI-E805) mounted thereto. These emitters include an integral lens, but a nonintegral lens system could also be provided for the emitter. These gallium-arsenide light-emitting diodes emit infrared light with a wavelength of 880 nanometers and can be switched on or off with activation times of about one microsecond. An opaque polymer block 18 that is 0.5 inches thick has ¼ inch diameter holes bored therethrough in corresponding relation to each emitter. A 0.040" polycarbonate sheet 19 (opaque except for a 0.25 inch circle above each emitter) overlies block 18. The structure of the mounting block thus provides an optical aperture positioned between the egg and the light emitters 17. In one embodiment, sheets available commercially for overhead projector transparencies are used. Likewise, the infrared light detector mounting block 21 is comprised of an opaque back plate 26 with the infrared detectors 27 (Texas Instruments Part number TSL261) mounted thereto. Integral lenses or non-integral lens systems could optionally be provided with the detectors. An opaque polymer block 28 that is 0.5 inches thick has ¾ inch diameter holes bored therethrough in corresponding relation to each emitter. A 0.04011 polycarbonate sheet 29 (opaque except for a 0.25 inch circle above each detector) overlies block 28. The polycarbonate sheets are a light-blocking, infrared transmissive polymer that have about 90% transmittance of wavelengths between 750 and 2000 manometers. The infrared light from the emitters has a wavelength near 880 nanometers. Thus, the sheets serve, at least in part, to block and filter ambient light. Again, the structure of the mounting block thus provides an optical aperture positioned between the egg and the light detectors 27. In all cases, opaque materials are preferably black. The apparatus is configured so that the distance "a" from the top of the egg to the polymer film 29 is from ½ to one inch, and so that the distance "b" from the bottom of the egg to the polymer film 19 is from ½ to one inch, with a distance of 0.5 inches preferred. Note that some egg flats and the variety of egg sizes cause this distance to typically range from ⅜ inch to one inch. The size of the viewed area on the egg is typically from about a 0.25 to about a 0.5 inch area, or from about 0.1 inches to about 0.3 inches in diameter. Smaller areas typically give better rejection of light reflected off of adjacent eggs.

Some of the photoemitters may be off set from the center line of the eggs so that they miss the conveyor belts. It is not necessary that their corresponding detectors be colinearly aligned with the emitters since the light entering the egg is diffused by the shell and contents. In operation, light from the emitter is projected as a 5 to 10 degree cone with a total light output in this cone of about 20 milliwatts. Typically the light reaches the egg in a circle about 0.5 inches in diameter and diffuses within the egg so that the entire egg is illuminated and glows. Clear eggs glow with a light level (or irradiance) approximately $10^4$ less than the illuminating irradiance, and live eggs glow with an irradiance about $10^5$ less than the illuminating irradiance.

Figure 7:
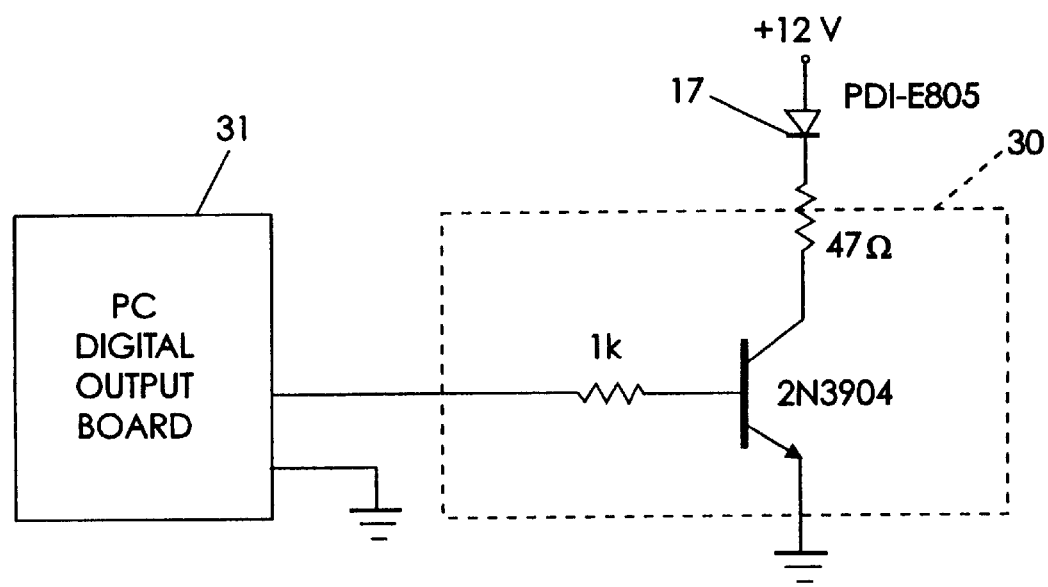
FIG. 7 is a schematic diagram of a computer driven light source.
Figure 8:
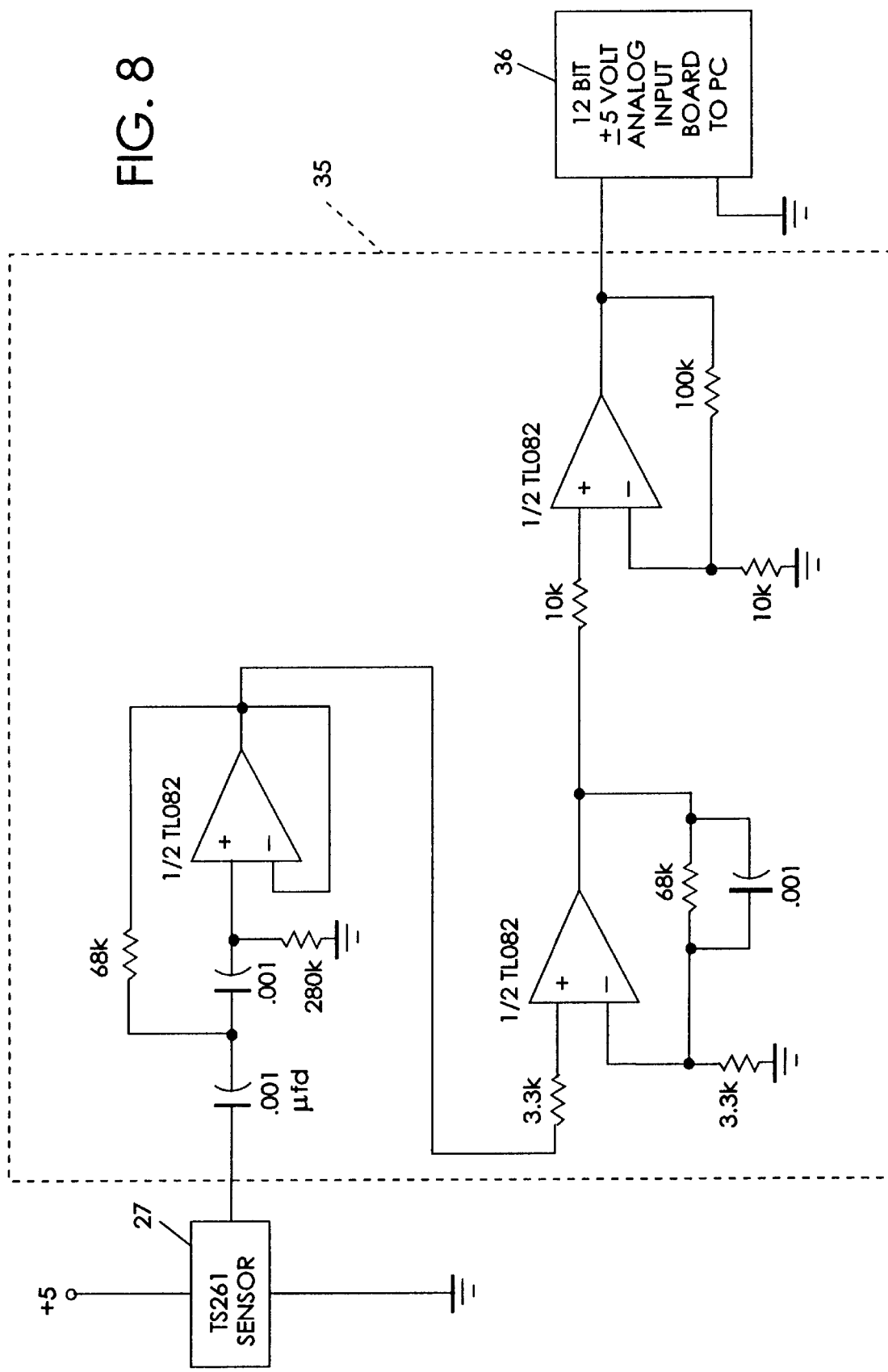
FIG. 8 is a schematic diagram of a light detector and corresponding filter, amplifier and computer input board.

FIG. 7 is a schematic diagram of the circuitry 30 corresponding to light source 17, with corresponding digital output board 31 installed in the personal computer (not shown: see FIG. 1), and FIG. 8 is a schematic diagram of the filter, amplifier and input circuitry 35 accompanying light detector 27, with a corresponding 12 bit±5 volt analog input board 36 installed in the personal computer. All is conventional circuitry, and numerous variations thereon will be readily apparent to those skilled in the art.

In operation of an apparatus as given above, each emitter is typically turned on for about 250 microseconds. The output of each photodetector is amplified by a bandwidth-limited filter (2 kHz high pass filter combined with a 1.0 kHz low pass filter). The filter maximizes detection of the 250 microsecond pulses of light from the photoemitters while minimizing noise from either electronic circuitry or stray light in the environment. The output from each filter is sampled about 120 microseconds after the corresponding emitter is turned on. The samples are digitized and recorded by the computer. A second sample is taken about 25 microseconds after the corresponding emitter is turned off. The off-light sample when subtracted from the on-light sample further improves rejection of ambient lighting around the identifier.

Figure 9:
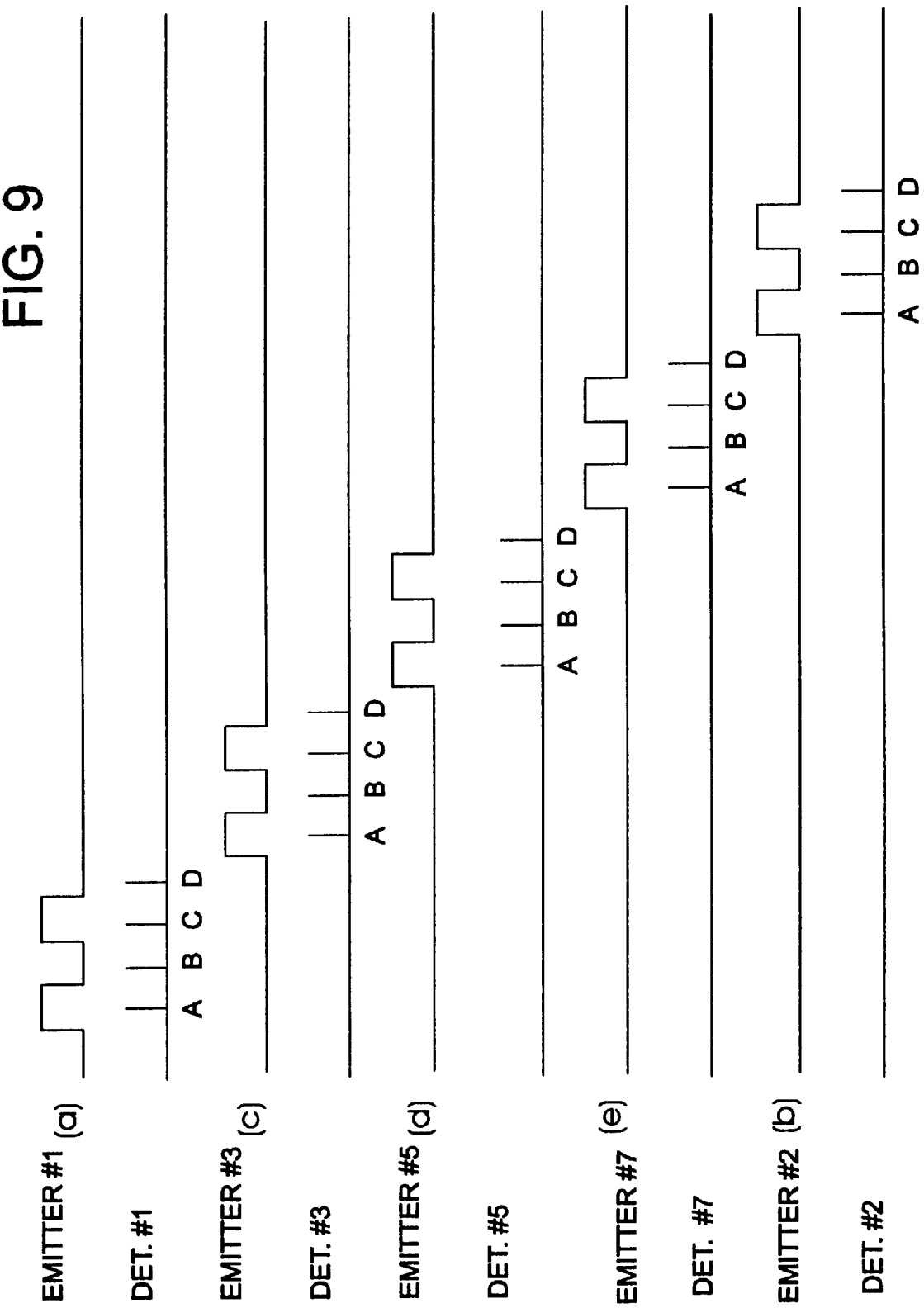
FIG. 9 is a diagram showing a pattern of cycling a row of light emitters and sampling the light detectors. Note that emitter and detector pairs 4 and 6 are not illustrated, but follow the pattern established by emitter and detector pairs 1, 2, 3, 5 and 7. Square pulses on emitter lines indicate times when emitters are active; peaks on detector lines indicate times when detectors are active. The cycling (on/off) of emitter 1 is indicated by waveform (a); the cycling of emitter 2 is indicated by waveform (b); the cycling of emitter 3 is indicated by waveform (c); the cycling of emitter 5 is indicated by waveform (d); and the cycling of emitter 7 is indicated by waveform (e).

The pattern of cycling the rows of emitters and sampling the detectors is shown in FIG. 9, where:

$$\text{Signal}_n = (A-B+C-D)/2 \text{ from detector}_n.$$

Typically several repetitions of the above process may be done to improve the accuracy of the data from each egg. Eggs pass between the light emitters and detectors on conveyor belts moving about 10 inches per second. At a belt speed of 10 inches per second and a sampling time of 7 milliseconds per row, each egg is scanned every $\frac{1}{14}$ of an inch. Two repetitions can be done in about 1000 microseconds, so that, in a row of seven eggs, all seven eggs in a row can be measured in less than 7 milliseconds. After each row is received, software partitions the eggs into live eggs, clear eggs, mid-dead eggs and missing eggs according to the amount of light passed through each egg. The processing begins by establishing that a full row has been received through an algorithm that finds rows by noticing the strong light received by most of the detectors between eggs. Preset cutoffs are used in conjunction with the minimum level of light received by each egg to make a live/dead/mid-dead classification, with clears being greater than 100 millivolts and lives being less than 50 millivolts. After eggs are identified as live, clear, mid-dead or missing, the results are displayed graphically on the PC computer's screen along with cumulative statistics for a group or flock of eggs.

In another embodiment of the light emitter mounting block 11, the diodes are mounted in an opaque polymer block 18 that positions the diodes and protects them from water and dust in the working environment. A flat sapphire window above each diode is transparent to the light from the diode. Similarly, the light detector mounting block 21 may be comprised of an opaque back plate 26 with lensed infrared detectors (IPL Part number IPL10530DAL) mounted thereto. An opaque polymer block 28 that is 0.6 inches thick has 0.33 inch diameter holes bored therethrough in corresponding relation to each emitter. A transparent sapphire window allows light passing through an egg to illuminate the detector above it. As described above, some of the photoemitters may be off set from the center line of the eggs so that they miss the conveyor belts.

Figure 13:
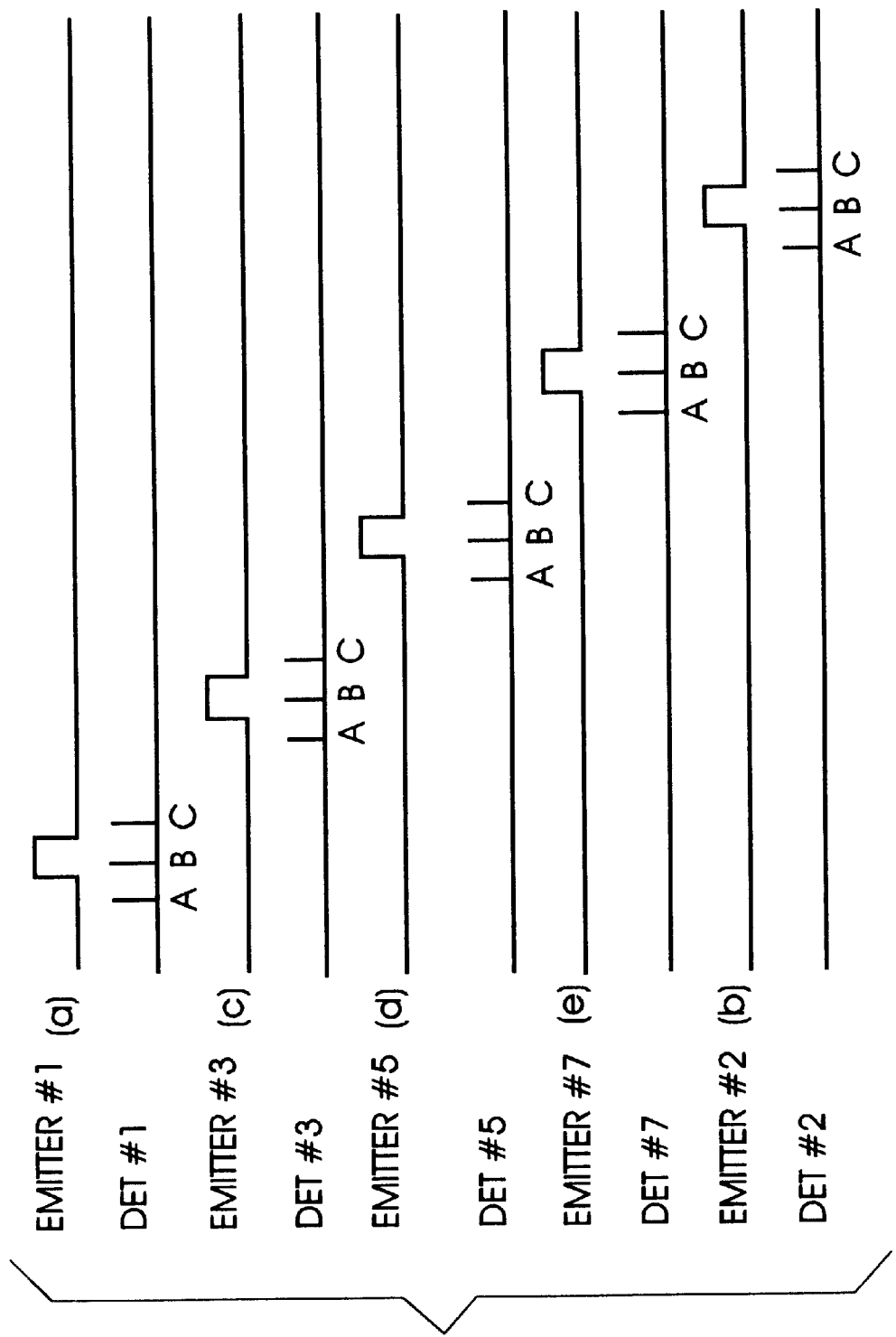
FIG. 13 is a diagram showing an alternate pattern of cycling a row of light emitters and sampling the light detectors. Note that emitter and detector pairs 4 and 6 are not illustrated, but follow the pattern established by emitter and detector pairs 1, 2, 3, 5 and 7. Square pulses on emitter lines indicate times when emitters are active; peaks on detector lines indicate times when detectors are active. The cycling (on/off) of emitter 1 is indicated by waveform (a); the cycling of emitter 2 is indicated by waveform (b); the cycling of emitter 3 is indicated by waveform (c); the cycling of emitter 5 is indicated by waveform (d); and the cycling of emitter 7 is indicated by waveform (e).

In another embodiment, in the operation of an apparatus as described above, each emitter is typically turned on for about 150 microseconds. The output from each detector is sampled just before and about 150 microseconds before and after the corresponding emitter is turned on. A third sample is taken about 150 microseconds after the corresponding emitter is turned off. The samples are digitized and recorded by the computer. The off-light samples are averaged and subtracted from the on-light sample to improve rejection of ambient lighting around the identifier. The pattern of cycling the rows of emitters and sampling the detectors is shown in FIG. 13, where:

$$\text{Signal}_n = (2B-A-C)/2 \text{ from detector}_n.$$

Sampling a row of seven eggs requires about 450 milliseconds per egg, or approximately 3 milliseconds. Eggs pass between the light emitters and detectors on conveyor belts moving about 10 inches per second. At a belt speed of 10 inches per second and a sampling interval of 5 milliseconds, each egg is scanned every $\frac{1}{20}^{th}$ of an inch. After each row is received, software partitions the eggs as described above. Preset cutoffs are used in conjunction with the minimum level of light received by each egg to classify the eggs, for example, with clears being greater than 35 millivolts and lives being less than 20 millivolts.

In normal operation, the front edge of an egg flat is located either by the flat moving up to a fixed stop or by a photo-optic device, also operatively associated with the computer, locating the front edge of the flat. Normally the row of illuminators and detectors is aligned with the front row of the flat at that time. The flat is then moved forward by the conveyor system while the row of detectors continuously scan the eggs. Software defines the passage of rows of eggs by the strong light that passes between eggs as the margin between rows moves past the detectors. The minimum light level recorded between successive row edges is used to discriminate clear from live eggs. Data from the entire flat is recorded for later processing to identify mid-dead eggs. As a check on the location of rows, the computer also monitors the condition of the stop (open or closed) as well as the running or stopped state of the conveyor motor.

Eggs identified as clear, dead and/or mid dead can be removed by any conventional method, including manually or by suction-type lifting devices as disclosed in U.S. Pat. No. 4,681,063, the disclosure of which is incorporated by reference herein in its entirety.

One aspect of the present invention combines an automated in ovo injection device with an apparatus for classifying each egg in a plurality of avian eggs as either suitable for injection or not suitable for injection. The classification device (or "classifier") is operatively associated with the injection device, so that only those eggs identified as suitable for injection are injected with a treatment substance.

The classification of eggs as suitable for injection (or "suitable") may be based on the identification of eggs as either fertile or non-fertile, with fertile eggs being suitable for injection. Alternatively, the classification may be based on the identification of eggs as either live (i.e., eggs that contain a living embryo) or non-live (i.e., infertile or containing a dead embryo), with live eggs being suitable for injection. As used herein, the term "non-live" egg refers to an egg that has either not been fertilized or that was fertilized but in which the avian embryo has died. As used herein, the term "dead" egg refers to an egg that contains an avian embryo that has died. "Non-live" eggs thus include both non-fertile and dead eggs. Non-live eggs will not hatch. Additionally, the classifying means may be designed to identify "empty eggs" (in which the internal contents have leaked out) as well as "missing eggs" (where the egg compartment passing through the apparatus does not contain any egg). Empty and missing eggs are classified as not suitable for injection.

Where classifying means are designed to distinguish infertile eggs ('clear eggs') from fertile eggs, and to classify fertile eggs as suitable for injection, it is recognized that eggs classified as fertile may include some dead eggs. The present methods of selectively injecting eggs identified as suitable for injection may equally well be described as a method of selectively not injecting eggs identified as unsuitable for injection, as will be apparent to one skilled in the art.

As used herein, the term "treatment substance" refers to a substance that is injected into an egg to achieve a desired result. Treatment substances include but are not limited to vaccines, antibiotics, vitamins, virus, and immunomodulatory substances. Vaccines designed for in ovo use to combat outbreaks of avian diseases in the hatched birds are commercially available. Typically the treatment substance is dispersed in a fluid medium, e.g., is a fluid or emulsion, or is a solid dissolved in a fluid, or a particulate dispersed or suspended in a fluid.

As used herein, the term "needle" or "injection needle" refers to an instrument designed to be inserted into an egg to deliver a treatment substance into the interior of the egg. A number of suitable needle designs will be apparent to those skilled in the art. The term "injection tool" as used herein refers to a device designed to both pierce the shell of an avian egg and inject a treatment substance therein. Injection tools may comprise a punch for making a hole in the egg shell, and an injection needle that is inserted through the hole made by the punch to inject a treatment substance in ovo. Various designs of injection tools, punches, and injection needles will be apparent to those in the art.

As used herein, "in ovo injection" refers to the placing of a substance within an egg prior to hatch. The substance may be placed within an extraembryonic compartment of the egg (e.g., yolk sac, amnion, allantois) or within the embryo itself. The site into which injection is achieved will vary depending on the substance injected and the outcome desired, as will be apparent to those skilled in the art.

Figure 10:
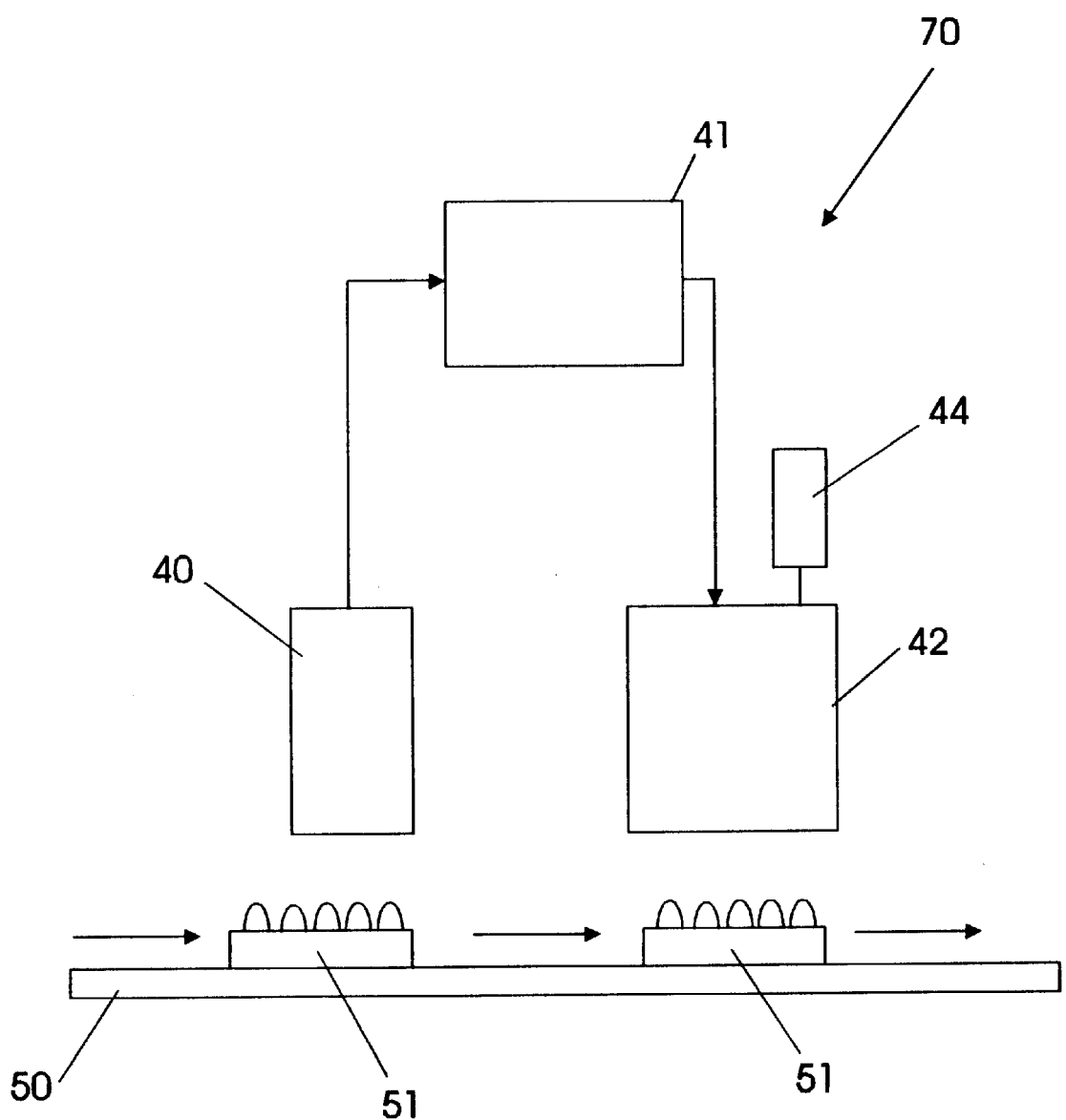
FIG. 10 is a schematic diagram of a selective injection device.

FIG. 10 schematically illustrates an apparatus (70) that can be used to carry out the selective injection methods of the present invention. In overview, with reference to FIG. 10, an apparatus (70) of the invention comprises: a classifier (40) for classifying eggs as either suitable for injection or as non-suitable for injection; a controller (41) for receiving signals from the classifier and for generating a selective injection signal based on the presence and relative position of each suitable egg; and an injector (42) associated with the controller for injecting only those eggs identified as suitable. The injector (42) comprises at least one reservoir (44) for holding the treatment substance to be injected into the eggs identified as suitable. A conveyor (50) is configured to move a plurality of eggs (for example, eggs contained in a commercial egg flat) past the classifier (40) and injector (42). The direction of travel of the eggs along the conveyors is indicated by arrows in FIG. 10.

Those skilled in the art will appreciate that many conveyor designs will be suitable for use in the present invention. The conveyor (50) may be in the form of guide rails designed to receive and hold an egg flat, or a conveyor belt upon which an egg flat can be placed. Conveyor belts or guide rails may include stops or guides that act to evenly space a plurality of egg flats along the conveying path.

As used herein, the "selective generation of an injection signal" (or the generation of a selective injection signal), refers to the generation by the controller of a signal that causes injection only of those eggs identified by the classifier as suitable for injection. As will be apparent to those skilled in the art, generation of a selective injection signal may be achieved by various approaches, including generating a signal that causes the injection of suitable eggs, or generating a signal that prevents the injection of non-suitable eggs.

A preferred injector for use in the methods described herein is the INOVOJECT® automated injection device (Embrex, Inc., Research Triangle Park, N.C.). However, any in ovo injection device capable of being operably connected, as described herein, to means for classifying eggs is suitable for use in the present methods. Suitable injection devices preferably are designed to operate in conjunction with commercial egg carrier devices or "flats", examples of which are described herein. Preferably, the eggs to be injected according to the present methods are carried in egg flats as described herein; however, as will be apparent to those skilled in the art, any means of presenting a plurality of eggs over time to the classifier for identification of suitable eggs can be used in the present methods. The eggs may pass one at a time under the classifier or, as described herein, the classifier may be configured so that a number of eggs can pass under the classifier simultaneously.

Preferably, the injector comprises a plurality of injection needles, to increase the speed of operation. The injector may comprise a plurality of injection needles which operate simultaneously or sequentially to inject a plurality of eggs, or alternatively may comprise a single injection needle used to inject a plurality of eggs.

Figure 11:
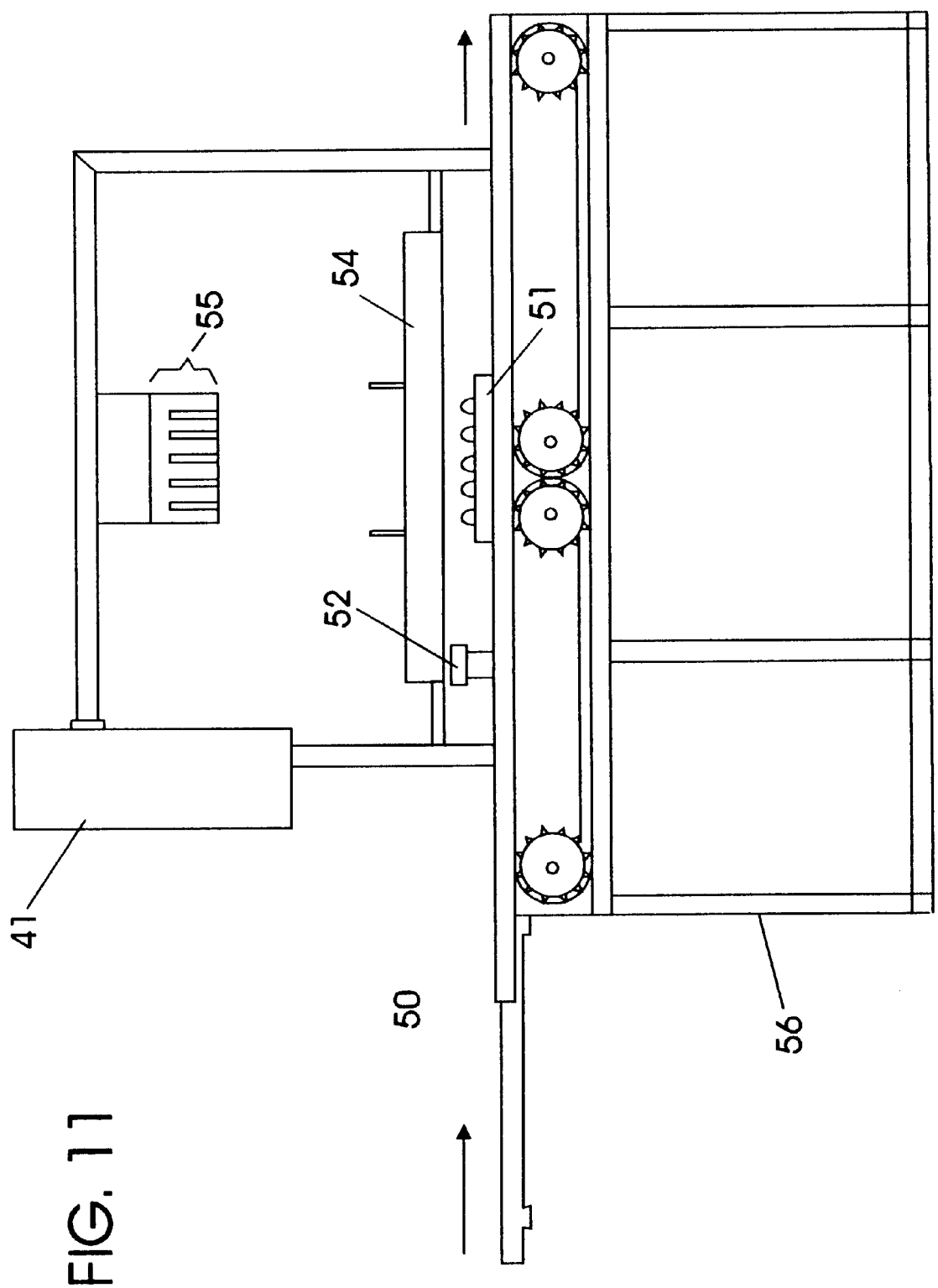
FIG. 11 is a side view of the selective injection device of FIG. 10.
Figure 12:
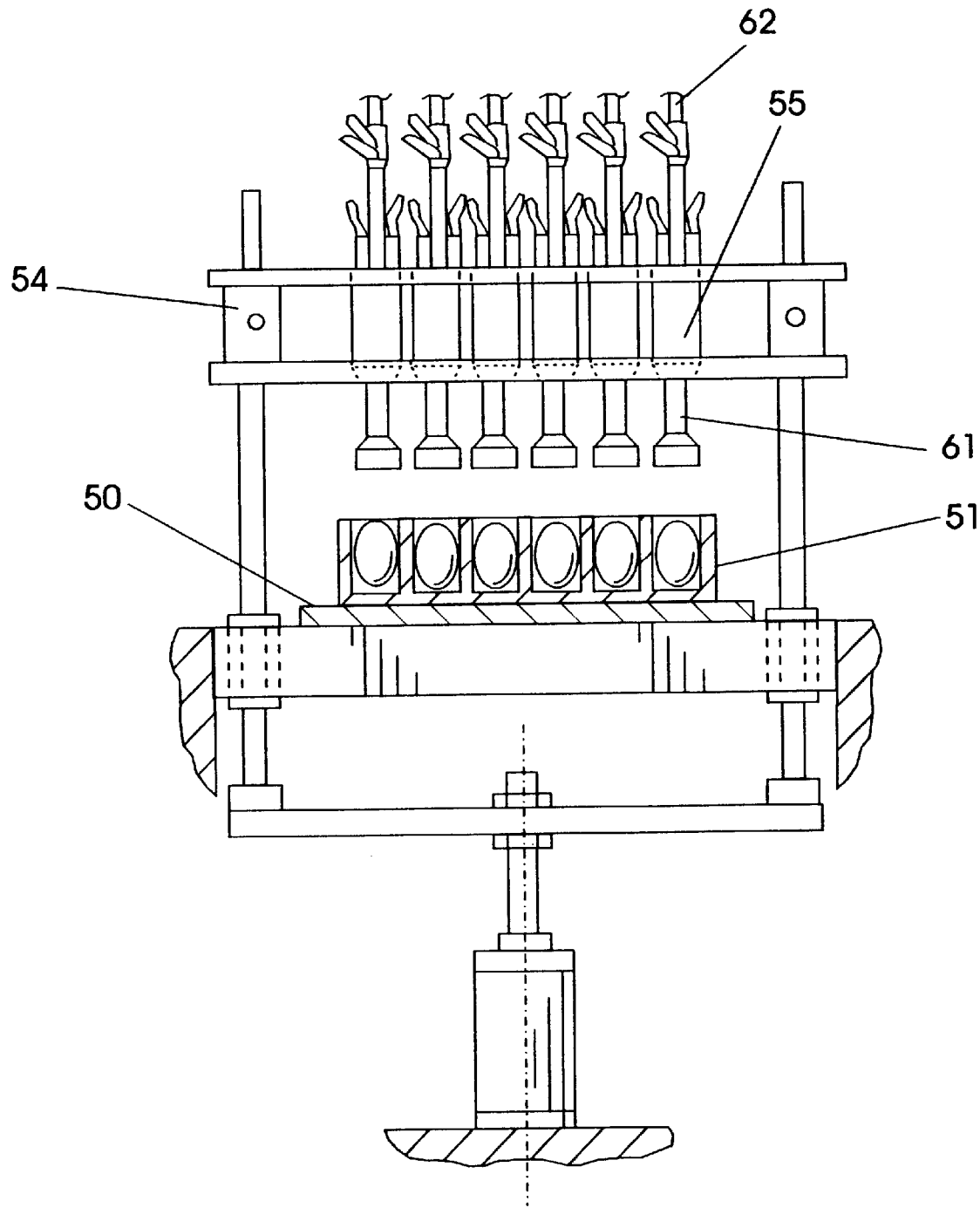
FIG. 12 is an enlarged side view of an injection head of the selective injection device of FIG. 11, wherein the injection head is aligned with a plurality of eggs contained within an egg flat.

As shown in FIG. 11, the injection device may comprise an injection head (54) in which the injection needles (not shown) are situated. The injection head or the injection needles are capable of movement in order to inject eggs. Each injection needle is in fluid connection with a reservoir containing the treatment substance to be injected. A single reservoir may supply all of the injection needles in the injection head, or multiple reservoirs may be utilized. An exemplary injection head is shown in FIG. 12, where conveyor (50) has aligned egg flat (51) with the injection head (54). Each injection needle (not shown) is housed in a guiding tube (61) designed to rest against the exterior of an egg. Each injection needle is operably connected to a fluid pump (55). Each fluid pump is in fluid connection with tubing (62), which is in fluid connection with a reservoir (not shown) containing the treatment substance. Suitable injection devices are described in U.S. Pat. No. 4,681,063 to Hebrank, and U.S. Pat. No. 4,903,635 to Hebrank.

As shown in FIG. 10, eggs may be conveyed past the classifier (40) and the injector (42) in a fixed array (i.e., in a fixed position relative to other eggs), so that signals generated by the classifier, when conveyed to the injector, result in injection only of those eggs identified as suitable by the classifier. In other words, the eggs are prevented from changing their position relative to other eggs while passing from the classifier to the injector. This may be accomplished, for example, by utilizing commercial egg flats to transport a plurality of eggs along the conveyor.

A preferred classifier for identifying eggs suitable for injection utilizes light that is pulsed or cycled at a frequency different from (and preferably higher than) ambient light, as described herein. However, those skilled in the art will appreciate that any automated method of distinguishing live from non-live eggs, or fertile from non-fertile eggs, and generating a signal to a controller for processing may be utilized. Methods of classifying eggs include those based on the temperature of the egg, or the quality or quantity of light that passes through an egg; see, e.g., U.S. Pat. No. 3,540,824

(Fonda and Chandler), U.S. Pat. No. 4,671,652 (van Asselt), U.S. Pat. No. 4,914,672 (Hebrank), U.S. Pat. No. 4,955,728 (Hebrank) and U.S. Pat. No. 5,017,003 (Keromnes and Breuil). See also Das and Evans, *Am. Soc. Agricultural Engineers,* 35:1335 (1992).

In an exemplary device, the step of classifying eggs as suitable for injection is accomplished using a light measuring system, in which light is transmitted through an egg and assessed by a light detector. The eggs are identified as either fertile (suitable for injection) or non-fertile (not suitable for injection). The light detectors are operatively connected to a controller (which may be a microprocessor or other programmable or non-programmable circuitry). Means for conveying a plurality of eggs past the light measuring system is situated so the each egg passes through the light measuring system and data is generated for each egg. The data collected by the light measuring system is provided to the controller for processing and storing data associated with each egg, and the controller generates a selective injection signal. The controller is operatively connected to the injection device so that individual eggs are injected based on the data collected by the light measuring system; injection occurs only where the data from the light measuring system indicates that the egg is fertile. The designation of an egg as "fertile" may be made by comparing the data generated by the light measuring system for that egg to a predetermined programmed standard, or to measurements provided by a control sample.

A preferred embodiment of the present device for the classification of eggs as suitable for injection, and the selective injection of suitable eggs, is schematically illustrated in FIG. 11. A conveyor (50) is configured to move an egg flat (51) (direction of travel indicated by arrow) past a light measuring system (52) designed to classify eggs as suitable or non-suitable. The light measuring system comprises a plurality of light emitters and associated light detectors configured so that light travels through each egg and is detected. Transmission of light through an egg is measured by a light detector, which is operatively connected to a controller (41). A signal is generated by the light detector that indicates whether the egg is suitable or non-suitable; the signal is transmitted to and received by the controller (41). The controller is operatively connected to an injection device comprising an injection head (54) and a plurality of fluid pumps (55). The injection head comprises a plurality of needles; each needle is aligned with one compartment of the egg flat (i.e., is aligned with the egg contained therein). Each fluid pump is in fluid communication with a reservoir containing treatment substance (not shown in FIG. 11) and is in fluid communication with an injection needle (tubing providing fluid connection means not shown in FIG. 11). The controller generates and transmits to the injection device a signal so that treatment substance is delivered in ovo only to those eggs identified as suitable for injection.

The selective delivery of treatment substance only to eggs identified as suitable can be accomplished by any of various means that will be apparent to those skilled in the art. Examples include, but are not limited to, individually controlled fluid pumps, e.g., solenoid-operated pumps; or individual valves that control the flow of treatment substance from a reservoir to an associated fluid pump. Alternatively, selective delivery of treatment substance may be accomplished by individual control of injection needles or egg shell punches, so that punches and/or needles do not enter those eggs identified as non-suitable.

The classifier may be designed so that eggs can pass by in an uninterrupted flow (e.g., see description of photodetector distinguisher device herein). Where the eggs must come to a halt to be injected, it will be apparent to those skilled in the art that the use of an apparatus comprising more than one injection head may be desirable to increase the speed of the overall operation. The conveyor may comprise a plurality of conveying sections capable of independent movement but operatively connected to each other, so that an item placed on the initial conveying section will pass to subsequent conveying sections automatically. One conveying section may pass egg flats under the classifier in a continuous flow, whereas a subsequent conveying section may be used to move an egg flat to a position aligned with an injection head and halt while the eggs are injected. Movement of the conveyor may be under guidance of programmed or computerized control means or manually controlled by an operator. In a preferred embodiment, the conveying means (50) is supported by a frame (56) which raises the conveying means to a height at which egg flats can be conveniently loaded.

A preferred embodiment of the present selective injection apparatus comprises an INOVOJECT® automated injection device (Embrex, Inc., Research Triangle Park, N.C.) combined with a classifying device that comprises a photodetector distinguisher device as described herein. The photodetector distinguisher is mounted on the INOVOJECT® device above the egg flat conveyor and in front of the injection head (relative to the direction of travel by the egg flat). As the egg flat moves from its initial position to a position underneath the injection head, the egg flat passes through the photodetector distinguisher so that each egg is identified as either suitable or non-suitable for injection. The photodetectors generate and send signals indicating the detection of suitable eggs to the controller. The controller generates signals which are transmitted to the injection device so that only those eggs identified as suitable are injected with the treatment substance.

The present invention is described in greater detail in the following non-limiting Examples.

EXAMPLE 1

Optical Candling with Cycled Light Source

To illustrate the invention, several chicken eggs were hand candled and then measured by the methodology of the invention. These results are shown in Table 1 below. This data was measured using the 880 nM IR light source and detector. Results show a range of 40 to 83 units for clears, 8 to 25 for mid-deads, and 5.7 to 6 for lives. The significant differences between the three categories of eggs demonstrates the reliable classification of eggs that is possible with the method of the invention.

TABLE 1

| Optical Candling with Cycled Light Source | | |
|---|---|---|
| Egg Number | Egg Type | Detector Output |
| 1 | clear or early dead | 83 |
| 2 | clear or early dead | 47 |
| 3 | clear or early dead | 98 |
| 4 | clear or early dead | 78 |
| 5 | clear or early dead | 40 |
| 6 | mid dead | 25 |
| 7 | mid dead | 15 |
| 8 | mid dead | 8 |
| 9 | live (day 17) | 6 |
| 10 | live (day 17) | 5.6 |
| 11 | live (day 17) | 6 |

TABLE 1-continued

Optical Candling with Cycled Light Source

| Egg Number | Egg Type | Detector Output |
|---|---|---|
| 12 | live (day 17) | 5.7 |
| 13 | live (day 17) | 5.7 |

EXAMPLE 2

Apparatus for Selective Injection

An apparatus for the selective injection of chicken eggs was constructed using a model JW84 INOVOJECT® (Embrex, Inc., Research Triangle Park, N.C.). A classification device or classifier was mounted to the JW84 INOVOJECT® frame; the classification device included an array of seven photoemitters and seven photodetectors configured to operate with a JAMESWAY 84 flat (twelve rows of seven eggs in each egg). The classifier used infrared light as described herein. The classifier was mounted on the INOVOJECT® frame above the INOVOJECT® conveyor and oriented so that each row of eggs in an egg flat traveled past the classifier before entering the injection head. The injection head included a bank of eighty-four 50-microliter solenoid operated pumps (built by BioChem, Inc.), each pump connected to a reservoir containing a fluid vaccine.

A control unit comprising a 40 MHZ, 386 computer (CTC P1) with RTD analog inputs and digital output boards was configured to receive and store data from the classifier, and to transmit a selective injection signal to each solenoid operated pump.

In operation, JAMESWAY 84 flats containing 84 chicken eggs were loaded onto the ENOVOJECT® conveyor belt. Each flat traveled past the classifier, and each egg passed between a light emitter and a light detector. Data was transmitted to the controller which, using preset cutoff levels, identified each egg as either suitable for injection (fertile) or not suitable for injection (infertile, empty or missing). The controller generated and transmitted a selective injection signal to each injection pump. Each egg was pierced by an INOVOJECT® injection tool, however, only those injection pumps associated with needles placed in fertile eggs dispensed vaccine. This system was able to inject approximately 45,000 eggs per hour.

The foregoing is illustrative of the present invention, and is not to be construed as limiting thereof. The invention is defined by the following claims, with equivalents of the claims to be included therein.

That which is claimed is:

1. An automated apparatus for selectively injecting avian eggs, comprising:
   classifier means for classifying an egg as suitable for injection or as not suitable for injection;
   signaling means for generating a classification signal that indicates whether an egg is suitable for injection or not suitable for injection, said signaling means operatively connected with said classifier means;
   conveying means for conveying a plurality of eggs past said classifier means;
   control means for controlling injection of each of said eggs, said control means receiving said classification signal from said signaling means and selectively generating an injection signal based on said classification signal;
   injection means for injecting said avian eggs operatively connected to said control means.

2. An apparatus according to claim 1, wherein said classifier means is capable of distinguishing between fertile eggs and infertile eggs.

3. An apparatus according to claim 1, wherein said classifier means is capable of distinguishing between live eggs and non-live eggs.

4. An automated apparatus for selectively injecting avian eggs, comprising:
   classifier means for classifying an egg as suitable for injection or as not suitable for injection;
   signaling means for generating a classification signal that indicates whether an egg is suitable for injection or not suitable for injection, said signaling means operatively connected with said classifier means;
   conveying means for conveying a plurality of eggs in an egg carrier past said classifier means;
   control means for controlling injection of each of said eggs, said control means receiving said classification signal from said signaling means and selectively generating an injection signal based on said classification signal;
   injection means for injecting said avian eggs, operatively connected to said control means;
   wherein said classifier means comprises:
     a light measuring system having a light source positioned on one side of said egg carrier and a light detector positioned on the other side of said egg carrier opposite said light source; and
     a switching circuit operatively associated with said light source for cycling the intensity of said light source at a frequency greater than 100 cycles per second.

5. An apparatus according to claim 4, wherein said light source is an infrared light source.

6. An apparatus according to claim 4, wherein said egg carrier is configured to carry said eggs between said light source and said light detector in noncontacting relationship therewith.

7. An apparatus according to claim 4, further comprising an aperture positioned in front of said light source.

8. An apparatus according to claim 4, further comprising a lens system positioned in front of said light source.

9. An apparatus according to claim 4, further comprising an aperture positioned in front of said light detector.

10. An apparatus according to claim 4, further comprising a lens system positioned in front of said light detector.

11. An apparatus according to claim 4, further comprising an electronic filter operatively associated with said light detector for distinguishing light emitted from said light source from ambient light.

12. An apparatus according to claim 4, further comprising an optical filter positioned in front of said light detector for filtering ambient light.

13. An apparatus according to claim 4, further comprising a drive system operatively associated with said egg carrier, said drive system configured to pass eggs between said light source and said light detector at a rate of at least one egg per second.

14. An apparatus according to claim 4, wherein said egg carrier is configured to carry at least two rows of eggs in side-by-side relationship to one another; and wherein said apparatus comprises a plurality of said light measuring systems positioned in operative association with each of said rows of eggs.

15. An apparatus according to claim 14, wherein said switching circuit cycles adjacent ones of said light sources at a time or frequency different from one another.

16. An apparatus according to claim 14, further comprising data collection means for collecting data associated with each of said eggs operatively associated with said light detectors, and wherein said switching circuit is operatively associated with said data collection means so that data is collected from each of said light detectors in a cycle corresponding to the cycle of the corresponding light source.

17. A method for selectively injecting, in a plurality of avian eggs, eggs suitable for injection, said method comprising:

(a) conveying a plurality of eggs past classifier means for classifying an egg as suitable for injection or as not suitable for injection;

(b) generating a classification signal for each of said plurality of eggs indicating whether said each egg is suitable for injection or is not suitable for injection;

(c) transmitting said classification signal to control means for controlling injection of each of said eggs;

(d) generating a selective injection signal from said control means based on said classification signal;

(e) transmitting said selective injection signal to injection means for injecting a substance into avian eggs, so that only those eggs indicated by said classification signal as suitable for injection are injected with said substance.

18. An apparatus according to claim 17, wherein said classifier means is capable of distinguishing between fertile eggs and infertile eggs.

19. An apparatus according to claim 17, wherein said classifier means is capable of distinguishing between live eggs and non-live eggs.

20. A method according to claim 17, wherein said steps (a) through (c) are repeated at a rate of at least one egg per second.

21. A method for selectively injecting, in a plurality of avian eggs, eggs suitable for injection, said method comprising:

(a) conveying a plurality of eggs past classifier means for classifying an egg as suitable for injection or as not suitable for injection;

(b) generating a classification signal for each of said plurality of eggs indicating whether said each egg is suitable for injection or not suitable for injection, by:

(i) providing a light source and a light detector in opposite facing relation to one another and configured so that at least one of said plurality of eggs conveyed by said conveying means passes between said light source and said light detector;

(ii) providing switching means for switching said light source at a frequency greater than 100 cycles per second; and (iii) detecting light that passes through said egg from said light source with said light detector.

(c) transmitting said classification signal to control means for controlling injection of each of said eggs;

(d) generating a selective injection signal from said control means based on said classification signal;

(e) transmitting said selective injection signal to injection means for injecting a substance into avian eggs, so that only those eggs indicated by said classification signal as suitable for injection are injected with said substance.

22. A method according to claim 21, wherein said light source is an infrared light source.

23. A method according to claim 21, wherein the egg is passed between said light source and said light detector without making contact therewith.

24. A method according to claim 21, further comprising the step of electronically filtering the signal detected by said light detector to distinguish light emitted from said light source from ambient light.

* * * * *

EX PARTE REEXAMINATION CERTIFICATE (8979th)
United States Patent
Hebrank et al.

(10) Number: US 5,900,929 C1
(45) Certificate Issued: *Apr. 24, 2012

(54) METHOD AND APPARATUS FOR SELECTIVELY INJECTING POULTRY EGGS

(75) Inventors: John H. Hebrank, Durham, NC (US); Daniel T. DePauw, Raleigh, NC (US)

(73) Assignee: Embrex, Inc., Research Triangle Park, NC (US)

Reexamination Request:
No. 90/010,747, Nov. 23, 2009

Reexamination Certificate for:
Patent No.: 5,900,929
Issued: May 4, 1999
Appl. No.: 09/008,664
Filed: Jan. 16, 1998

( * ) Notice: This patent is subject to a terminal disclaimer.

Related U.S. Application Data

(63) Continuation-in-part of application No. 08/785,689, filed on Jan. 17, 1997, now Pat. No. 5,745,228.

(51) Int. Cl.
*G01N 33/08* (2006.01)

(52) U.S. Cl. .......................................... 356/52; 356/53
(58) Field of Classification Search ......................... None
See application file for complete search history.

(56) References Cited

To view the complete listing of prior art documents cited during the proceeding for Reexamination Control Number 90/010,747, please refer to the USPTO's public Patent Application Information Retrieval (PAIR) system under the Display References tab.

*Primary Examiner* — M. Sager

(57) ABSTRACT

A method for distinguishing live from dead poultry eggs comprises: (a) providing a light source (preferably an infrared light source) and a light detector in opposite facing relation to one another; (b) passing an egg between the light source and light detector; (c) switching the light source at a frequency greater than 100 cycles per second while passing the egg between the light source and the light detector; and (d) detecting light that passes through the egg from the light source with the light detector. Preferably, the egg is passed between the light source and the light detector without making contact therewith. And the method preferably further comprises the step of electronically filtering the signal detected by the light detector to distinguish light emitted from the light source from ambient light. Steps (b) through (d) may be repeated at a rate of at least one egg per second. Apparatus for carrying out the foregoing method is also provided. A method of selectively injecting only eggs identified as suitable for injection, and apparatus for carrying out such a method, is described.

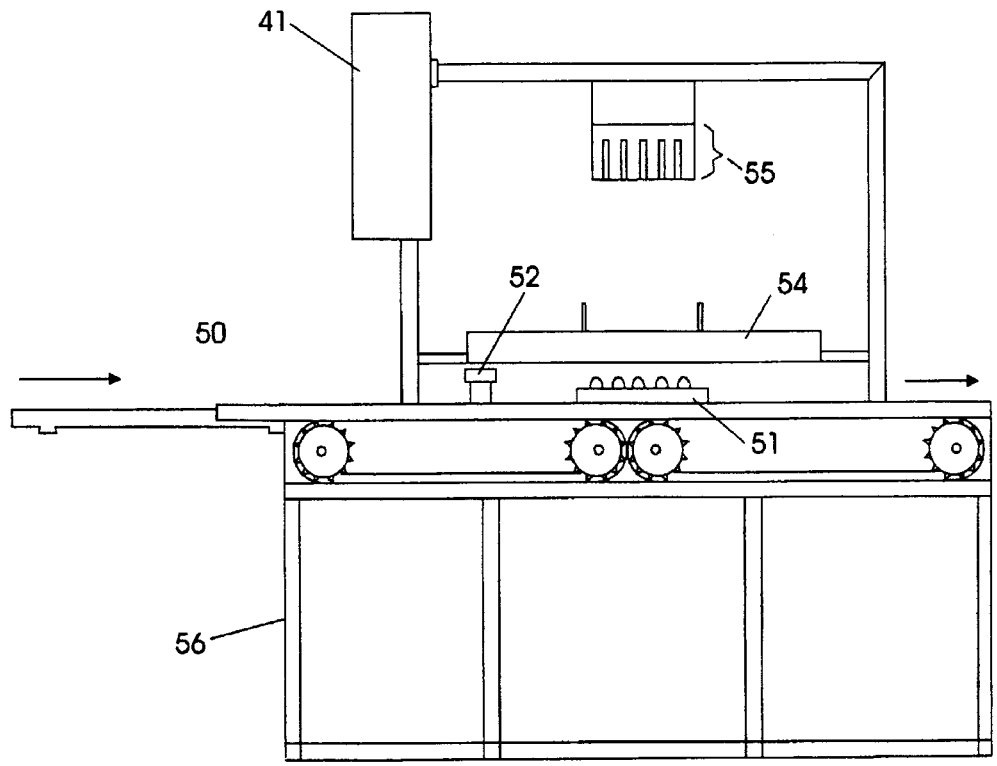

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-24 is confirmed.

New claims 25-34 are added and determined to be patentable.

*25. An automated apparatus for selectively injecting avian eggs, comprising:*

*classifier means for classifying an egg as suitable for injection or as not suitable for injection, eggs classified as not suitable for injection including eggs identified by the classifier as being one of a non-live egg and a missing egg;*

*signaling means for generating a classification signal that indicates whether an egg is suitable for injection or not suitable for injection, said signaling means operatively connected with said classifier means;*

*conveying means for conveying a plurality of eggs past said classifier means;*

*control means for controlling injection of each of said eggs, said control means receiving said classification signal from said signaling means and selectively generating an injection signal based on said classification signal;*

*injection means for injecting said avian eggs, based on said injection signal, operatively connected to said control means, so that only those eggs indicated by said classification signal as suitable for injection are injected and eggs indicated by said classification signal as non-live eggs and missing eggs are not injected.*

*26. A method for selectively injecting, in a plurality of avian eggs, eggs suitable for injection, said method comprising:*

*(a) conveying a plurality of eggs past classifier means for classifying an egg as suitable for injection or as not suitable for injection, eggs classified as not suitable for injection including eggs identified by the classifier as being one of a non-live egg and a missing egg;*

*(b) generating a classification signal for each of said plurality of eggs indicating whether said each egg is suitable for injection or is not suitable for injection;*

*(c) transmitting said classification signal to control means for controlling injection of each of said eggs;*

*(d) generating a selective injection signal from said control means based on said classification signal;*

*(e) transmitting said selective injection signal to injection means for injecting a substance into avian eggs, so that only those eggs indicated by said classification signal as suitable for injection are injected with said substance, and eggs indicated by said classification signal as non-live eggs and missing eggs are not injected with said substance.*

*27. An automated apparatus for selectively injecting avian eggs, comprising:*

*classifier means for classifying an egg as suitable for injection or as not suitable for injection;*

*signaling means for generating a classification signal that indicates whether an egg is suitable for injection or not suitable for injection, said signaling means operatively connected with said classifier means;*

*conveying means for conveying a plurality of eggs past said classifier means;*

*control means for controlling injection of each of said eggs, said control means receiving said classification signal from said signaling means and selectively generating an injection signal based on said classification signal;*

*injection means for injecting a vaccine substance into said avian eggs, based on said injection signal, operatively connected to said control means, so that only those eggs indicated by said classification signal as suitable for injection are injected and eggs indicated by said classification signal as not suitable for injection are not injected.*

*28. A method for selectively injecting, in a plurality of avian eggs, eggs suitable for injection, said method comprising:*

*(a) conveying a plurality of eggs past classifier means for classifying an egg as suitable for injection or as not suitable for injection;*

*(b) generating a classification signal for each of said plurality of eggs indicating whether said each egg is suitable for injection or is not suitable for injection;*

*(c) transmitting said classification signal to control means for controlling injection of each of said eggs;*

*(d) generating a selective injection signal from said control means based on said classification signal;*

*(e) transmitting said selective injection signal to injection means for injecting a vaccine substance into avian eggs, so that only those eggs indicated by said classification signal as suitable for injection are injected with said substance, and eggs indicated by said classification signal as not suitable for injection are not injected with said vaccine substance.*

*29. An automated apparatus for selectively injecting avian eggs, comprising:*

*classifier means for classifying an egg as suitable for injection or as not suitable for injection, the eggs classified as not suitable for injection including non-live eggs;*

*signaling means for generating a classification signal that indicates whether an egg is suitable for injection or not suitable for injection, said signaling means operatively connected with said classifier means;*

*conveying means for conveying a plurality of eggs past said classifier means;*

*control means for controlling injection of each of said eggs, said control means receiving said classification signal from said signaling means and selectively generating an injection signal based on said classification signal;*

*injection means for injecting said avian eggs, based on said injection signal, operatively connected to said control means, so that only those eggs indicated by said classification signal as suitable for injection are injected and non-live eggs are not injected.*

30. A method for selectively injecting, in a plurality of avian eggs, eggs suitable for injection, said method comprising:
(a) conveying a plurality of eggs past classifier means for classifying an egg as suitable for injection or as not suitable for injection, the eggs not suitable for injection including non-live eggs;
(b) generating a classification signal for each of said plurality of eggs indicating whether said each egg is suitable for injection or is not suitable for injection;
(c) transmitting said classification signal to control means for controlling injection of each of said eggs;
(d) generating a selective injection signal from said control means based on said classification signal;
(e) transmitting said selective injection signal to injection means for injecting a vaccine substance into avian eggs, so that only those eggs indicated by said classification signal as suitable for injection are injected with said substance, and non-live eggs are not injected.

31. An automated apparatus for selectively injecting avian eggs, comprising:
classifier means for classifying an egg as suitable for injection or as not suitable for injection;
signaling means for generating a classification signal that indicates whether an egg is suitable for injection or not suitable for injection, said signaling means operatively connected with said classifier means;
conveying means for conveying a plurality of eggs past said classifier means;
control means for controlling injection of each of said eggs, said control means receiving said classfication signal from said signaling means and selectively generating an injection signal based on said classification signal;
injection means for injecting said avian eggs operatively connected to said control means, so that of the plurality of eggs, only those eggs indicated by said classification signal as suitable for injection are injected with a substance, and those eggs indicated by said classification signal as not suitable for injection remain in said plurality of eggs and are not injected with said substance.

32. A method for selectively injecting, in a plurality of avian eggs, eggs suitable for injection, said method comprising:
(a) conveying a plurality of eggs past classifier means for classifying an egg as suitable injection or as not suitable for injection;
(b) generating a classification signal for each of said plurality of eggs indicating whether said each egg is suitable for injection or is not suitable for injection;
(c) transmitting said classification signal to control means for controlling injection of each of said eggs;
(d) generating a selective injection signal from said control means based on said classification signal;
(e) transmitting said selective injection signal to injection means for injecting a substance into avian eggs, so that of the plurality of eggs, only those eggs indicated by said classification signal as suitable for injection are injected with said substance, and those eggs indicated by said classification signal as not suitable for injection remain in said plurality of eggs and are not injected with said substance.

33. An automated apparatus for selectively injecting avian eggs, comprising:
classifier means for classifying an egg as suitable for injection or as not suitable for injection;
signaling means for generating a classification signal that indicates whether an egg is suitable for injection or not suitable for injection, said signaling means operatively connected with said classifier means;
conveying means for conveying a plurality of eggs in a fixed array past said classifier means;
control means for controlling injection of each of said eggs, said control means receiving said classification signal from said signaling means and selectively generating an injection signal based on said classification signal;
injection means for injecting said avian eggs operatively connected to said control means, so that of the plurality of eggs, only those eggs indicated by said classification signal as suitable for injection are injected with a substance while those eggs indicated by said classification signal as not suitable for injection remain in said fixed array without being removed, and are not injected with said substance.

34. A method for selectively injecting, in a plurality of avian eggs, eggs suitable for injection, said method comprising:
(a) conveying a plurality of eggs in a fixed array past classifier means for classifying an egg as suitable for injection or as not suitable for injection;
(b) generating a classification signal for each of said plurality of eggs indicating whether said each egg is suitable for injection or is not suitable for injection;
(c) transmitting said classification signal to control means for controlling injection of each of said eggs;
(d) generating a selective injection signal from said control means based on said classification signal;
(e) conveying the plurality of eggs in the fixed array past injection means; and
(f) transmitting said selective injection signal to the injection means for injecting a substance into avian eggs, so that of the plurality of eggs, only those eggs indicated by said classification signal as suitable for injection are injected with said substance while those eggs indicated by said classification signal as not suitable for injection remain in said fixed array without being removed, and are not injected with said substance.

* * * * *